US009204906B2

(12) United States Patent
Cannestra (10) Patent No.: US 9,204,906 B2
(45) Date of Patent: Dec. 8, 2015

(54) POSTERIOR CERVICAL FUSION SYSTEM AND TECHNIQUES (75) Inventor: Andrew F. Cannestra, Jacksonville, FL (US)

(73) Assignee: NuVasive, Inc., San Diego, CA (US)

( * ) Notice: Subject to any disclaimer, the term of this patent is extended or adjusted under 35 U.S.C. 154(b) by 382 days.

(21) Appl. No.: 13/503,050

(22) PCT Filed: Oct. 21, 2010

(86) PCT No.: PCT/US2010/053497
§ 371 (c)(1),
(2), (4) Date: Apr. 20, 2012

(87) PCT Pub. No.: WO2011/050140
PCT Pub. Date: Apr. 28, 2011

(65) Prior Publication Data
US 2012/0215259 A1     Aug. 23, 2012

Related U.S. Application Data (60) Provisional application No. 61/253,886, filed on Oct. 22, 2009.

(51) Int. Cl.
*A61B 17/90*     (2006.01)
*A61B 17/70*     (2006.01)
*A61B 17/17*     (2006.01)
*A61B 17/16*     (2006.01)

(52) U.S. Cl.
CPC ......... *A61B 17/7064* (2013.01); *A61B 17/1757* (2013.01); *A61B 17/1671* (2013.01)

(58) Field of Classification Search
CPC .... A61B 17/56; A61B 17/88; A61B 17/7064; A61B 17/7074; A61B 2017/0256; A61B 17/17; A61B 17/7076; A61B 17/7083; A61B 17/15; A61B 17/025; A61B 17/7062; A61B 17/66; A61B 17/7079; A61F 2/46
USPC ............ 606/247, 86 R, 90, 96, 99, 104, 105, 606/86 A, 914, 916
See application file for complete search history.

(56) References Cited

U.S. PATENT DOCUMENTS

| 4,907,577 | A | * | 3/1990 | Wu ................................ 606/87 |
| 5,099,494 | A | | 3/1992 | Kingston et al. |
| 5,395,317 | A | | 3/1995 | Kambin |
| 5,431,658 | A | * | 7/1995 | Moskovich .................... 606/99 |
| 5,464,864 | A | | 11/1995 | King et al. |
| 5,531,751 | A | | 7/1996 | Schultheiss et al. |
| 5,568,742 | A | | 10/1996 | Bauer |
| 5,571,109 | A | * | 11/1996 | Bertagnoli ................. 606/86 A |
| 5,586,840 | A | | 12/1996 | Nishio et al. |
| 5,662,197 | A | | 9/1997 | Tabe |

(Continued)

FOREIGN PATENT DOCUMENTS

| CN | 101433479 | 2/2012 |
| EP | 077159 | 4/1983 |

(Continued)

*Primary Examiner* — Jerry Cumberledge
(74) *Attorney, Agent, or Firm* — Jonathan Spangler; Jennifer Russell (57) ABSTRACT

A posterior cervical fusion surgery assembly and method. The assembly includes a sled adapted to be positioned in a facet joint and two receivers slidably mounted on the sled. The receivers are adapted to support surgical instruments such as a drill, a tap, and a screw. The sled assists in orienting the instruments at a desired angle with respect to the spine.

9 Claims, 12 Drawing Sheets

(56) References Cited

U.S. PATENT DOCUMENTS

| | | | |
|---|---|---|---|
| 5,669,915 A | 9/1997 | Caspar et al. | |
| 5,762,629 A | 6/1998 | Kambin | |
| 5,837,209 A | 11/1998 | Saegusa | |
| 6,063,088 A * | 5/2000 | Winslow | 606/86 A |
| 6,113,602 A | 9/2000 | Sand | |
| 6,162,239 A | 12/2000 | Manhes | |
| 6,228,022 B1 | 5/2001 | Friesem et al. | |
| 6,267,763 B1 * | 7/2001 | Castro | 606/86 A |
| 6,270,498 B1 | 8/2001 | Michelson | |
| 6,428,541 B1 | 8/2002 | Boyd et al. | |
| 6,436,098 B1 | 8/2002 | Michelson | |
| 6,440,139 B2 | 8/2002 | Michelson | |
| 6,443,987 B1 | 9/2002 | Bryan | |
| 6,447,512 B1 | 9/2002 | Landry et al. | |
| 6,508,827 B1 | 1/2003 | Manhes | |
| 6,540,753 B2 | 4/2003 | Cohen | |
| 6,575,981 B1 | 6/2003 | Boyd et al. | |
| 6,648,895 B2 | 11/2003 | Burkus et al. | |
| 6,656,205 B1 | 12/2003 | Manhes | |
| 6,692,434 B2 | 2/2004 | Ritland | |
| 6,725,080 B2 | 4/2004 | Melkent et al. | |
| 6,743,234 B2 | 6/2004 | Burkus et al. | |
| 6,929,647 B2 | 8/2005 | Cohen | |
| 6,960,216 B2 | 11/2005 | Kolb et al. | |
| 6,969,392 B2 | 11/2005 | Gitis et al. | |
| 7,033,362 B2 | 4/2006 | McGahan et al. | |
| 7,074,226 B2 | 7/2006 | Roehm, III et al. | |
| 7,083,623 B2 | 8/2006 | Michelson | |
| 7,118,576 B2 | 10/2006 | Gitis et al. | |
| 7,153,304 B2 | 12/2006 | Robie et al. | |
| 7,166,073 B2 * | 1/2007 | Ritland | 600/210 |
| 7,226,452 B2 | 6/2007 | Zubok et al. | |
| 7,314,851 B2 | 1/2008 | Meesilpa et al. | |
| 7,338,527 B2 * | 3/2008 | Blatt et al. | 623/17.15 |
| 7,396,360 B2 * | 7/2008 | Lieberman | 606/247 |
| 7,399,303 B2 | 7/2008 | Michelson | |
| 7,431,722 B1 | 10/2008 | Michelson | |
| 7,491,205 B1 | 2/2009 | Michelson | |
| 7,507,242 B2 | 3/2009 | Triplett et al. | |
| 7,527,629 B2 * | 5/2009 | Link et al. | 606/87 |
| 7,569,054 B2 | 8/2009 | Michelson | |
| 7,591,851 B2 | 9/2009 | Winslow et al. | |
| 7,615,079 B2 | 11/2009 | Flickinger et al. | |
| 7,635,370 B2 | 12/2009 | Michelson | |
| 7,722,619 B2 | 5/2010 | Michelson | |
| 7,731,721 B2 | 6/2010 | Rathbun et al. | |
| 7,740,635 B2 | 6/2010 | Lieberman | |
| 7,776,046 B2 | 8/2010 | Boyd et al. | |
| 7,776,047 B2 | 8/2010 | Fanger et al. | |
| 7,780,675 B2 | 8/2010 | Schneid | |
| 7,824,431 B2 * | 11/2010 | McCormack | 606/279 |
| 7,837,713 B2 * | 11/2010 | Petersen | 606/247 |
| 7,909,829 B2 | 3/2011 | Patel et al. | |
| 7,918,878 B2 | 4/2011 | Songer et al. | |
| 7,935,123 B2 | 5/2011 | Fanger et al. | |
| 7,959,677 B2 | 6/2011 | Landry et al. | |
| 8,016,831 B2 * | 9/2011 | Gil et al. | 606/86 A |
| 8,025,678 B2 | 9/2011 | Reynolds et al. | |
| 8,075,591 B2 | 12/2011 | Ludwig et al. | |
| 8,105,362 B2 | 1/2012 | Duarte | |
| 8,109,934 B2 | 2/2012 | Guenther et al. | |
| 8,123,786 B2 | 2/2012 | Lins | |
| 8,142,440 B2 | 3/2012 | Dace et al. | |
| 8,152,714 B2 | 4/2012 | Garcia-Bengochea et al. | |
| 8,172,854 B2 | 5/2012 | Blain et al. | |
| 8,231,661 B2 * | 7/2012 | Carls et al. | 606/279 |
| 8,282,642 B2 | 10/2012 | McClintock et al. | |
| 8,298,235 B2 * | 10/2012 | Grinberg et al. | 606/86 A |
| 8,323,292 B2 * | 12/2012 | Dudasik et al. | 606/96 |
| 8,328,814 B2 | 12/2012 | Klingseis et al. | |
| 8,328,815 B2 | 12/2012 | Farr et al. | |
| 8,337,500 B2 | 12/2012 | Bertagnoli et al. | |
| 8,366,748 B2 * | 2/2013 | Kleiner | 606/279 |
| 8,394,107 B2 | 3/2013 | Fanger et al. | |
| 8,425,530 B2 | 4/2013 | Winslow et al. | |
| 8,465,495 B2 | 6/2013 | Belliard | |
| 8,491,585 B2 | 7/2013 | Hannani et al. | |
| 8,523,865 B2 | 9/2013 | Reglos et al. | |
| 8,579,909 B2 | 11/2013 | Burkus et al. | |
| 8,641,719 B2 | 2/2014 | Gephart et al. | |
| 8,663,293 B2 | 3/2014 | Assell et al. | |
| 2002/0138079 A1 | 9/2002 | Cohen | |
| 2002/0161366 A1 * | 10/2002 | Robie et al. | 606/61 |
| 2003/0195520 A1 | 10/2003 | Boyd et al. | |
| 2005/0159756 A1 | 7/2005 | Ray | |
| 2005/0261770 A1 | 11/2005 | Kuiper et al. | |
| 2006/0200156 A1 | 9/2006 | Taha et al. | |
| 2006/0235391 A1 | 10/2006 | Sutterlin, III | |
| 2006/0247633 A1 * | 11/2006 | Winslow et al. | 606/61 |
| 2007/0123905 A1 | 5/2007 | Schneid | |
| 2007/0123985 A1 * | 5/2007 | Errico et al. | 623/17.11 |
| 2007/0135814 A1 | 6/2007 | Farris | |
| 2007/0233150 A1 | 10/2007 | Blain et al. | |
| 2008/0161810 A1 * | 7/2008 | Melkent | 606/79 |
| 2008/0167655 A1 | 7/2008 | Wang et al. | |
| 2009/0062857 A1 | 3/2009 | Ramsay et al. | |
| 2009/0062918 A1 | 3/2009 | Wang et al. | |
| 2009/0138091 A1 * | 5/2009 | Ray | 623/17.16 |
| 2009/0177237 A1 | 7/2009 | Zucherman et al. | |
| 2009/0234397 A1 * | 9/2009 | Petersen | 606/86 R |
| 2010/0023013 A1 * | 1/2010 | Flickinger et al. | 606/79 |
| 2010/0121378 A1 * | 5/2010 | Malek | 606/247 |
| 2010/0145391 A1 * | 6/2010 | Kleiner | 606/279 |
| 2010/0262200 A1 | 10/2010 | Ray, III et al. | |
| 2010/0268228 A1 | 10/2010 | Petersen | |
| 2010/0324560 A1 | 12/2010 | Suda | |
| 2011/0054537 A1 | 3/2011 | Miller et al. | |
| 2011/0118593 A1 | 5/2011 | Melkent et al. | |
| 2011/0307061 A1 | 12/2011 | Assell et al. | |
| 2012/0022597 A1 | 1/2012 | Gephart et al. | |
| 2012/0083849 A1 | 4/2012 | Neubardt | |
| 2012/0089191 A1 | 4/2012 | Altarac et al. | |
| 2012/0136392 A1 | 5/2012 | Keegan et al. | |
| 2012/0253316 A1 | 10/2012 | Oktavec et al. | |
| 2012/0253353 A1 | 10/2012 | McBride | |
| 2012/0265250 A1 | 10/2012 | Ali | |
| 2012/0271312 A1 | 10/2012 | Jansen | |
| 2012/0271357 A1 | 10/2012 | Arthur et al. | |
| 2012/0277801 A1 | 11/2012 | Marik et al. | |
| 2013/0012955 A1 | 1/2013 | Lin | |
| 2013/0033220 A1 | 2/2013 | Ueda | |
| 2013/0103036 A1 | 4/2013 | McGhie | |
| 2013/0110183 A1 | 5/2013 | Duggal et al. | |
| 2013/0123848 A1 | 5/2013 | Duggal et al. | |
| 2013/0211462 A1 | 8/2013 | Walker | |
| 2013/0310839 A1 * | 11/2013 | McCormack et al. | 606/90 |
| 2013/0310942 A1 | 11/2013 | Abdou | |
| 2014/0025121 A1 | 1/2014 | Foley et al. | |

FOREIGN PATENT DOCUMENTS

| | | |
|---|---|---|
| EP | 1923007 | 5/2008 |
| WO | 9522285 | 8/1995 |
| WO | 03020137 | 3/2003 |
| WO | 2008085445 | 7/2008 |
| WO | 2012024162 | 2/2012 |
| WO | 2013058737 | 4/2013 |

* cited by examiner

POSTERIOR CERVICAL FUSION SYSTEM AND TECHNIQUES

BACKGROUND OF THE INVENTION

The present invention relates to posterior cervical fusion instrumentation and to posterior cervical fusion surgery.

The facet joint or "zygapophysial" joint is a synovial joint between the superior articular process of one vertebra and the inferior articular process of the vertebra directly above it. There are two facet joints in each spinal motion segment (right and left). The biomechanical function of each pair of facet joints is to guide and limit movement of the spinal motion segment. These functions can be disrupted by degeneration, dislocation, fracture, injury, instability from trauma, osteoarthritis, and surgery.

Posterior cervical fusion surgery has become a common procedure for the treatment of degenerative disease of the cervical spine. In such surgery, fusion hardware, including plates and/or screws, are installed along the cervical spine to stabilize the bones, thereby facilitating fusion of the neck. Posterior cervical fusion has been shown to stabilize the cervical spine after decompression and eliminate the long term risks of destabilization over time. However, current fusion hardware has considerable limitations due to the significant amount of soft tissue dissection required to place the hardware. While improved instruments and techniques have been developed for lumbar spine surgery, relatively fewer improvements have been developed in posterior cervical spine surgery.

Application of existing lumbar spine techniques to the cervical spine presents specific challenges that prohibit the simple modification of these techniques. For example, the anatomy of the cervical spine does not allow the safe placement of guide wires due to the vulnerability of the cervical spinal cord. Similarly, the presence of lateral masses and underlying vertebral arteries prohibit the use of canulated hardware.

SUMMARY OF THE INVENTION

The present invention overcomes the above noted problems, providing a unique method, hardware and technique to place posterior cervical spine screws.

According to one embodiment, a screw insertion technique includes inserting a screw system during open surgery or while using minimally invasive techniques. The screw insertion technique may also be used in a purely percutaneous fashion or through a tubular or expandable minimally invasive retractor system. The technique uses the facet joint to guide the screws into position. A spatula or "facet sled" is inserted within the facet joint under radiographic guidance. Once the sled is in place, the screws can be guided along the sled device enabling the placement of the screws based on the patient's natural anatomy. By placing the "sled" as a guide in the facet joint, the joint itself provides the trajectory for the screws to then be inserted. The screws will therefore have the appropriate cranial-caudal trajectory to improve accuracy for screw placement. The screws can be attached to towers similar to those used in lumbar systems to allow for insertion of the rod.

In another embodiment, the screw and tower design may be adapted to mate with the sled system for guidance into the facet joint.

The present invention has distinct advantages over prior art posterior screw systems. First, the invention provides a technique and assembly for placing screws in the posterior cervical spine. Second, the sled provides an accurate trajectory along the facet joint, which automatically provides the appropriate trajectory for each screw and reduces the likelihood of inaccurately placed screws in the superior/inferior trajectory.

These and other objects, advantages, and features of the invention will be more fully understood and appreciated by reference to the description of the current embodiments and the drawings.

DESCRIPTION OF THE CURRENT EMBODIMENTS

Figure 1:
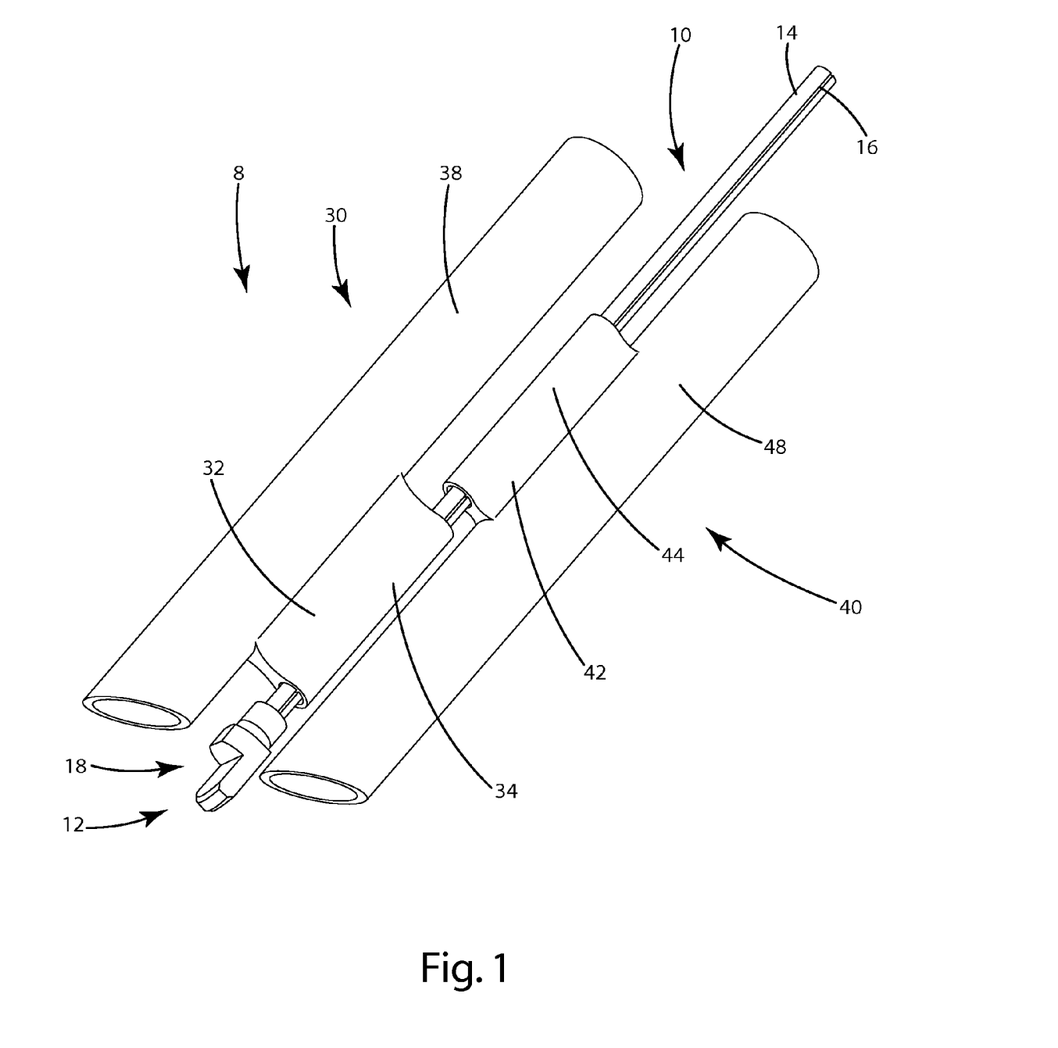
FIG. 1 is a perspective view of a posterior cervical screw insertion assembly in accordance with a first embodiment of the present invention.
Figure 6:
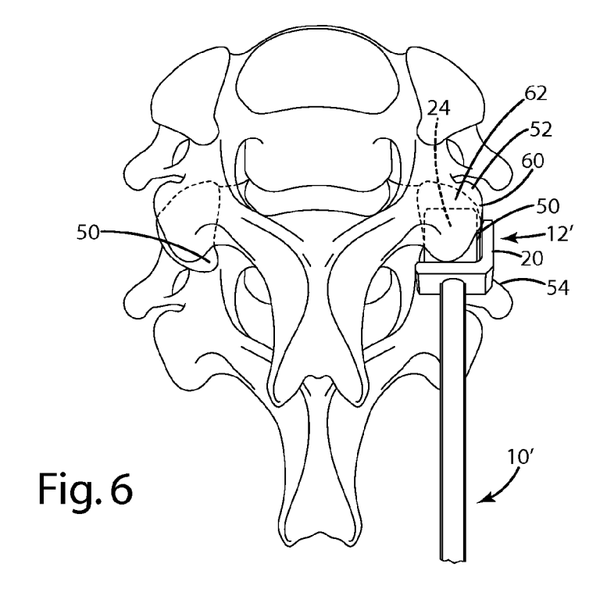
FIG. 6 is a posterior perspective view of a facet sled inserted into a facet joint.

An assembly for inserting posterior cervical screws is illustrated in FIG. 1 and is generally designated 8. The assembly 8 includes a facet sled or guide 10 having an end 12 that is adapted to be inserted within the facet joint 50 of a patient between a first vertebra 52 and a second vertebra 54. The end 12 may include a posterior guide or ridge 18 to limit the depth of insertion. As shown in FIG. 6, the facet sled 10' may also include lateral guides or ridges 20 to prevent medial migration during insertion. The facet sled 10 also includes an elongated handle 14 joined with and extending outward from the end 12.

Two current embodiments are disclosed in this application. In the first embodiment, shown in FIG. 1, the assembly 8 includes a superior cylindrical extension 30, positioned substantially above the handle 14, and an inferior cylindrical extension 40, positioned substantially below the handle 14. As used in this context, the terms "above" and "below" are in reference to the handle 14 when the end 12 is inserted into the facet joint 50 between the first vertebra 52 and the second vertebra 54 and the patient is upright. In other words, "above" indicates a direction from the handle generally upward toward a patient's head, but away from the patient's body and "below" indicates a direction from the handle generally downward away from a patient's head but towards the patient's body.

As shown in FIG. 1, the superior cylindrical extension 30 and inferior cylindrical extension 40 are slidably coupled to the facet sled handle 14. The cylindrical extensions 30, 40 include elongated receptacles 38, 48, which are adapted to receive and guide the drill 200, tap and screws 70 with attached screw towers or extensions 72. Although the terms "cylindrical extension" and "elongated tube" may be used in this application, the extensions 30, 40 and tubes 38, 48 may be virtually any shape that will satisfy the functionality of the extension and tube.

Figure 3:
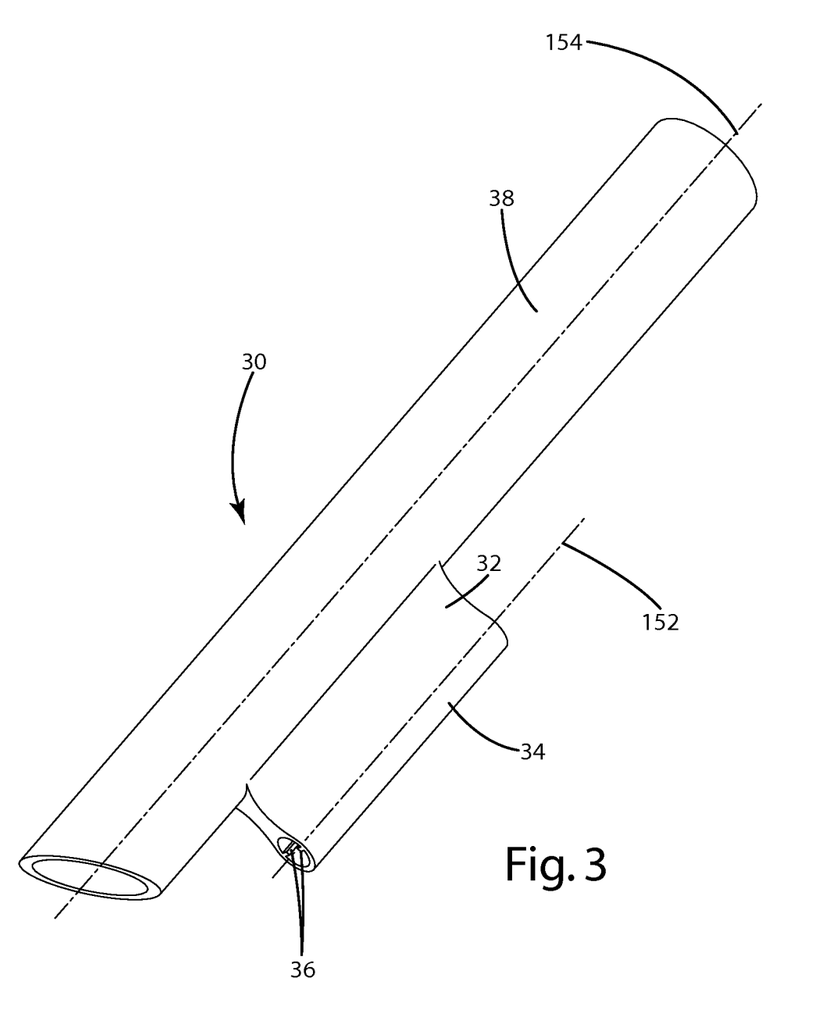
FIG. 3 is a perspective view of a superior cylindrical extension.
Figure 4:
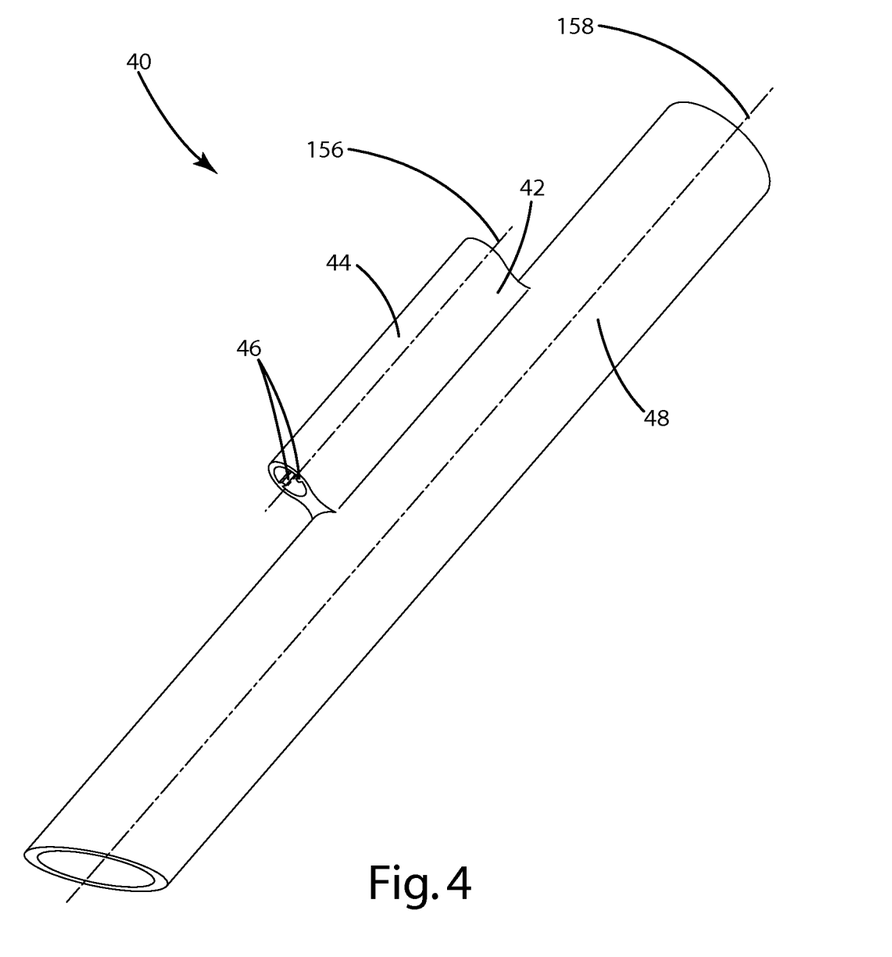
FIG. 4 is a perspective view of an inferior cylindrical extension.
Figure 5:
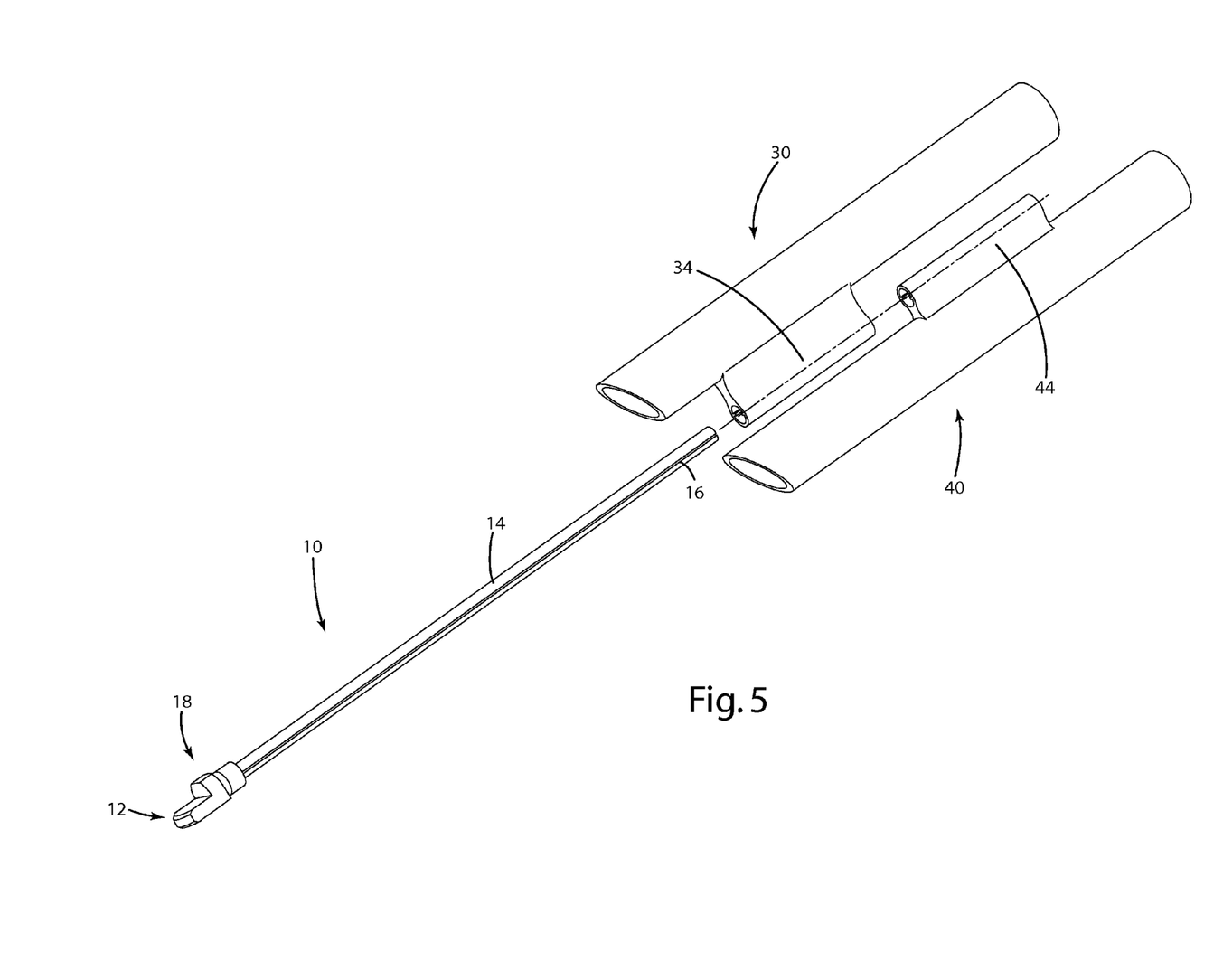
FIG. 5. is a perspective view of a superior cylindrical extension and an inferior cylindrical extension aligned with a handle of a facet sled.

As shown in FIGS. 3-5, the cylindrical extensions 30, 40 have offset guide members 32, 42, which mate with and travel down the facet handle 14. The offset of both the superior cylindrical extension 30 and the inferior cylindrical extension 40 from the handle 14 may be variable in size and/or angle to change the offset and angular position of the screw 70 relative to the facet sled 10. The insertion of the facet sled 10 into the facet joint 50 may allow the handle 14 of the facet sled 10 to establish the proper trajectory along which the screw towers 72 and other surgical instruments can travel to properly insert the screws 70 into the patient's spine 100.

Figures 13, 14:
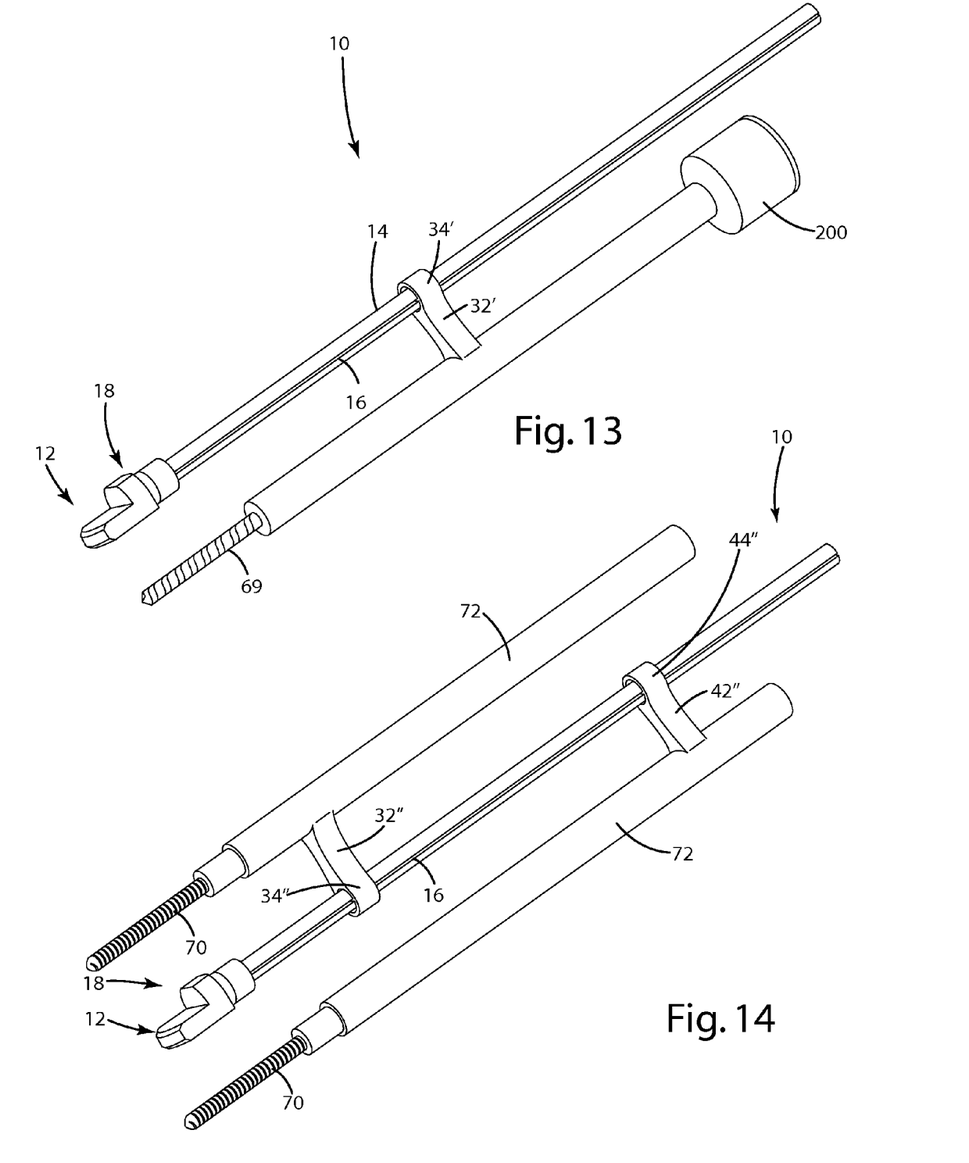
FIG. 13 is a perspective view of a facet sled and a drill in accordance with a second embodiment of the invention.
FIG. 14 is a perspective view of a facet sled and two screw towers in accordance with the second embodiment of the invention.

In the second embodiment, shown in FIGS. 13-14, the surgical instruments slidably engage the facet handle 14. In this embodiment, the assembly 8 may include at least one screw tower or extension 72, which is adapted to support a screw 70 for insertion into the patient's spine 100. Extending from the screw tower 72 is at least one guide member 32", 42", which engages and slides along the handle 14. The insertion of the facet sled 10 into the facet joint 50 allows the handle 14 of the facet sled to establish the proper trajectory along which the screw towers 72 and other surgical instruments can travel to properly insert the screws 70 into the patient's spine 100.

I. Structure

Figure 2:
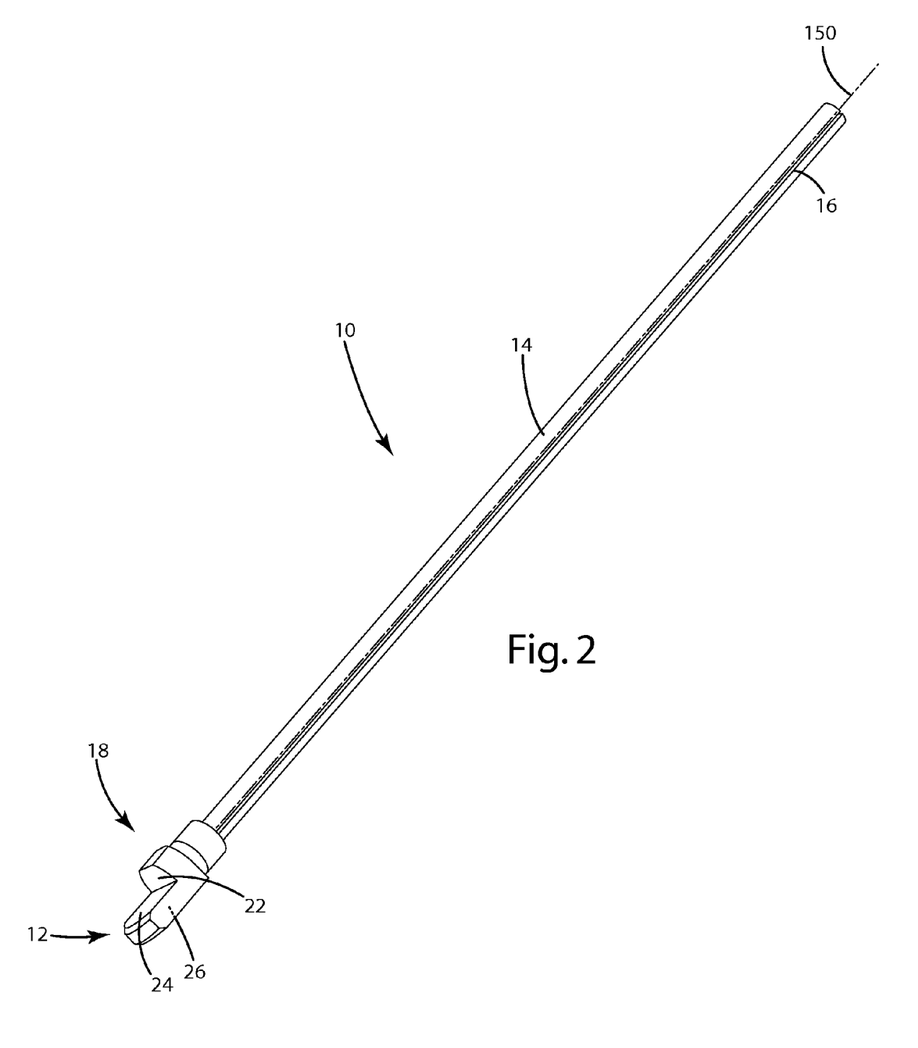
FIG. 2 is a perspective view of a facet sled.

The facet sled 10 may be formed in any shape and size suitable to allow the sled 10 to be inserted into the facet joint 50 of the patient. As shown in FIG. 2, the end 12 of the facet sled is generally flat and is sized to slide between the vertebrae 52, 54 of the patient. The end 12 may optionally be tapered to further facilitate insertion between the vertebrae 52, 54. The end 12 includes a top surface 24, which is adapted to engage a top surface 56 of the facet joint 50, formed by vertebra 52, and a bottom surface 26, which is adapted to engage a bottom surface 58 of the facet joint 50, formed by vertebra 54 (see FIG. 7). At least a portion of the top surface of the sled 24 and/or bottom surface of the sled 26 may include rasping surfaces in order to decorticate the joint surface and promote arthrodesis.

A different configuration of the facet sled 10' and more specifically, a different configuration of the sled end 12', is shown in FIGS. 6-9. As shown in FIG. 6, a lateral guide 20 may be positioned along a side edge of the end 12' and may have a greater thickness and shorter length than the end 12', i.e. the lateral guide 20 may not extend as far outward from the handle 14 as does the end 12'. The lateral guide 20 may be adapted to engage a side surface 60 of the vertebra 52, as shown in FIG. 6. As a result of the lateral guide 20, there may be right and left sided facet sleds 10'. To improve versatility, the lateral guide 20 may be removable such that one end 12' may be capable of converting between a right and left sided facet sled 10'. The posterior guide 18 engages a front surface 62 of vertebra 52 with stop surface 22, which prevents the instrument from being inserted too deeply within the facet joint 50, as shown in FIG. 6. The sled end 12' may be movable medially and laterally (left and right in FIG. 6) to allow a user to position the handle at a desired medial/lateral angle about the patient's spine. The stop surface 22 may be positioned substantially perpendicularly to the lateral guide 20 to allow the user to select an appropriate medial/lateral angle, or the stop surface 22 may be positioned at various other angles with respect to lateral guide 20 such that the medial/lateral angle is predetermined when the sled end 12' is inserted into a facet joint 50. Optionally, the desired medial/lateral angle may be approximately 30°, which may create a diagonal trajectory into the vertebrae 52, 54. Further optionally, there may be rasping surfaces included on other surfaces of the sled 10. Further optionally, there may be a multitude of facet sleds 10 or removable ends 12 ranging in sizes to allow dilation of the facet joint 50 and rasping/cleaning of the surface prior to placement of the facet sled 10 or end 12 for screw insertion.

The handle 14 is elongated and is adapted to extend outward from a patient's spine 100 when the end 12 is inserted into the patient's facet joint 50. The handle 14 slidably receives, supports and guides the cylindrical extensions 30, 40 via placement of the handle receivers 34, 44 onto handle 14. The handle 14 defines at least one track 16 that is adapted to receive and guide the cylindrical extensions 30, 40. As shown in FIG. 2, the track 16 can be formed as a recess or notch in the surface of the handle 14 and can optionally extend lengthwise along the entire length of the handle 14. In this configuration, the cylindrical extensions 30, 40 may include handle receivers 34, 44 that include bosses or tongues 36, 46. The tongues 36, 46 may optionally extend lengthwise along the entire length of the inner surface of the handle receivers 34, 44 to match the track 16.

The tongues 36, 46 may be received within the track 16. More specifically, the tongues 36, 46 may be received by the same track 16 or separate tracks 16 on handle 14. Optionally, the track 16 may be positioned only in a selected location or in multiple locations along the handle 14. The track 16 and tongues 36, 46 cooperate to maintain the angular position of the handle receivers 34, 44, and therefore the angular position of the cylindrical extensions 30, 40, about a longitudinal axis 150 of the handle 14. Further optionally, different cylindrical extensions 30, 40 or different handle receivers 34, 44 may include tongues 36, 46 that position the cylindrical extensions 30, 40 at different angles about the longitudinal axis 150 of the handle 14 to accommodate different bone structures and patient needs. Further optionally, any suitable means for maintaining the angular position of the cylindrical extensions 30, 40 about the longitudinal axis 150 of the handle 14 may be used. As shown in FIG. 2, the handle 14 may extend in the same plane as the top surface 24 and bottom surface 26 of the end 12, so that the handle 14 can establish an accurate trajectory for the handle receivers 34, 44 and for the cylindrical extensions 30, 40. The facet sled 10, which may include the end 12, the posterior guide 18, the handle 14 and the lateral guide 20 can be integrally fabricated in a single piece, or could alternatively be fabricated from multiple pieces.

The cylindrical extensions 30, 40 can be formed in any suitable shape to support and guide the surgical instruments. As shown in FIGS. 3-4, the cylindrical extensions 30, 40 may include elongated receptacles 38, 48 to support and guide the surgical instruments. The elongated receptacles 38, 48 each have a longitudinal axis 154, 158, which may generally be referred to as the longitudinal axes of the cylindrical extensions 30, 40. In the embodiment of FIGS. 3-4, the elongated receptacles are shown as elongated tubes 38, 48. The elongated tubes 38, 48 may be attached to the handle receivers 34, 44 with guide members 32, 42.

The guide members 32, 42 may be joined with the elongated tubes 38, 48 and the handle receivers 34, 44 in any suitable manner. For example, the guide members 32, 42 may be integrally formed, welded, adhered or releasably attached to the elongated tubes 38, 48 and the handle receivers 34, 44. Various sizes of interchangeable guide members 32, 42 or various cylindrical extensions 30, 40 with various sizes of permanently placed guide members 32, 42 may provide various distances between the facet joint 50 and the screw placement. Further optionally, various guide members 32, 42 may place the elongated tubes 38, 48 at various angles with respect to the handle, such that the cylindrical extension 30, 40 or the guide member 32, 42 may be additionally selected based on a desired angle. The guide members 32, 42 may be of any configuration that will adequately support the elongated tubes 38, 48 with respect to the handle receivers 34, 44. For example, the guide members 32, 42 may be formed as tubular members extending generally perpendicularly from the elongated tubes 38, 48. Optionally, the guide members 32, 42 may also be a single narrow connecting member as shown in FIGS. 3-4. Further optionally, the guide members 32, 42 may be more than one narrow connecting member. The use of the handle receivers 34, 44 and guide members 32, 42 may assist in keeping the elongated tubes 38, 48 parallel to the handle 14 when the end 12 is within the facet joint 50, which is generally considered a proper trajectory for the drill 200, tap and screws 70 during a posterior cervical fusion surgery.

Figure 9:
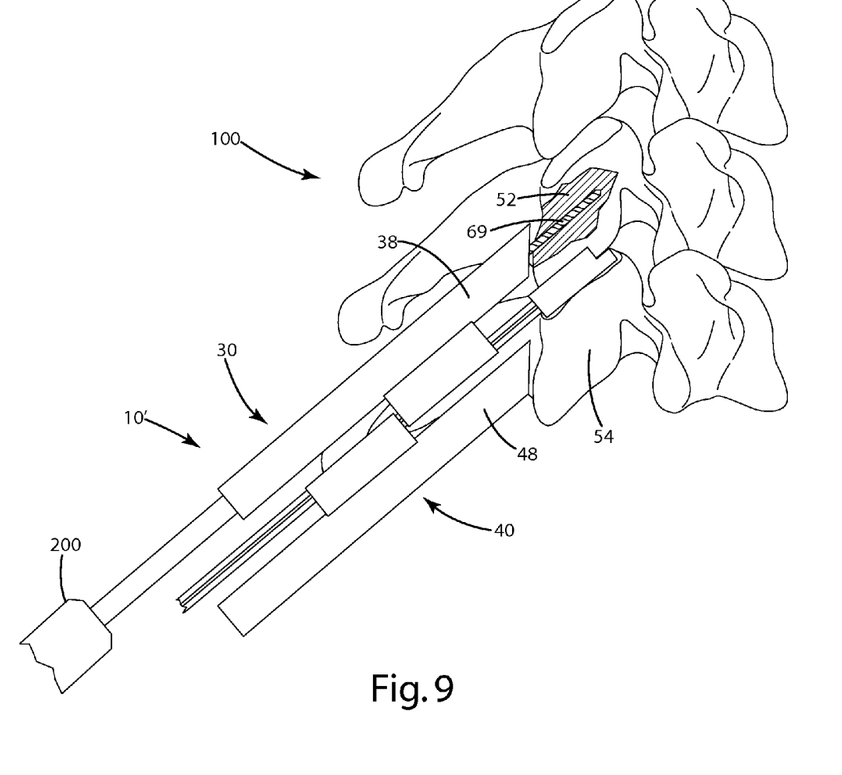
FIG. 9 is a side view of a facet sled inserted into a facet joint with a superior and an inferior cylindrical extension in place and a drill placed in the superior extension.
Figure 10:
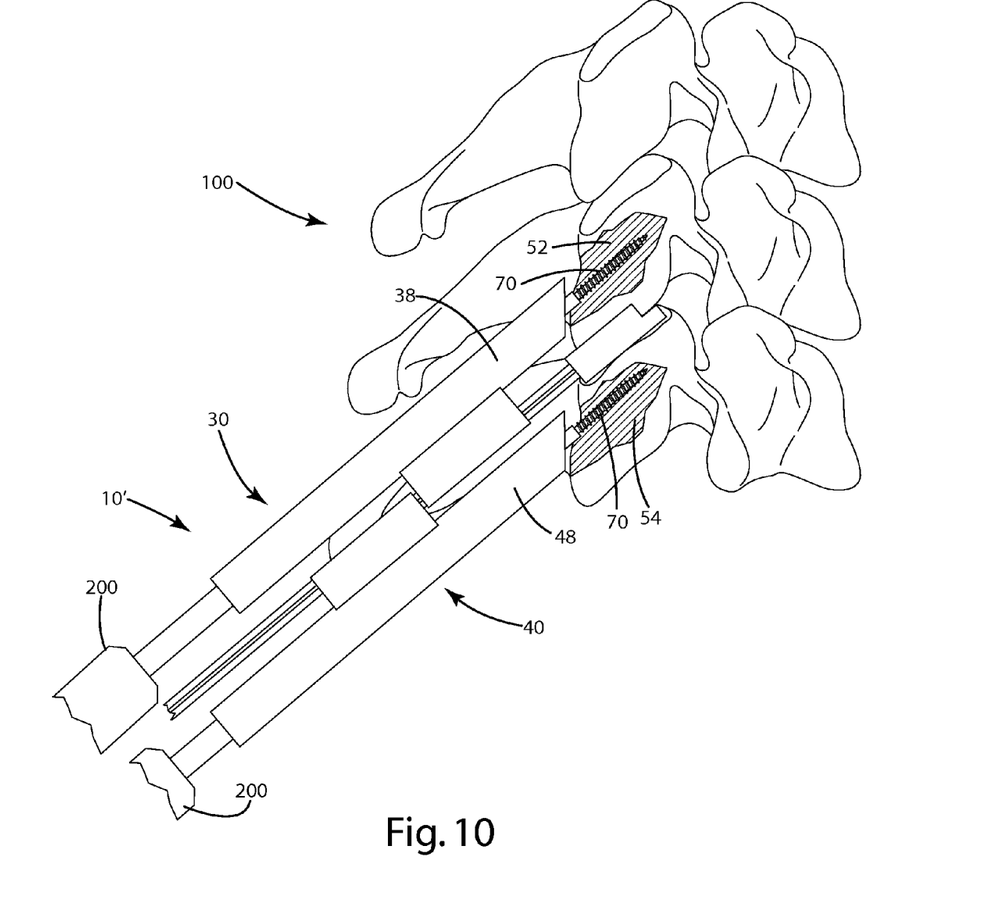
FIG. 10 is a side view of a facet sled inserted into a facet joint with a superior and an inferior cylindrical extension in place and screws placed through the extensions and into the vertebrae.
Figure 11:
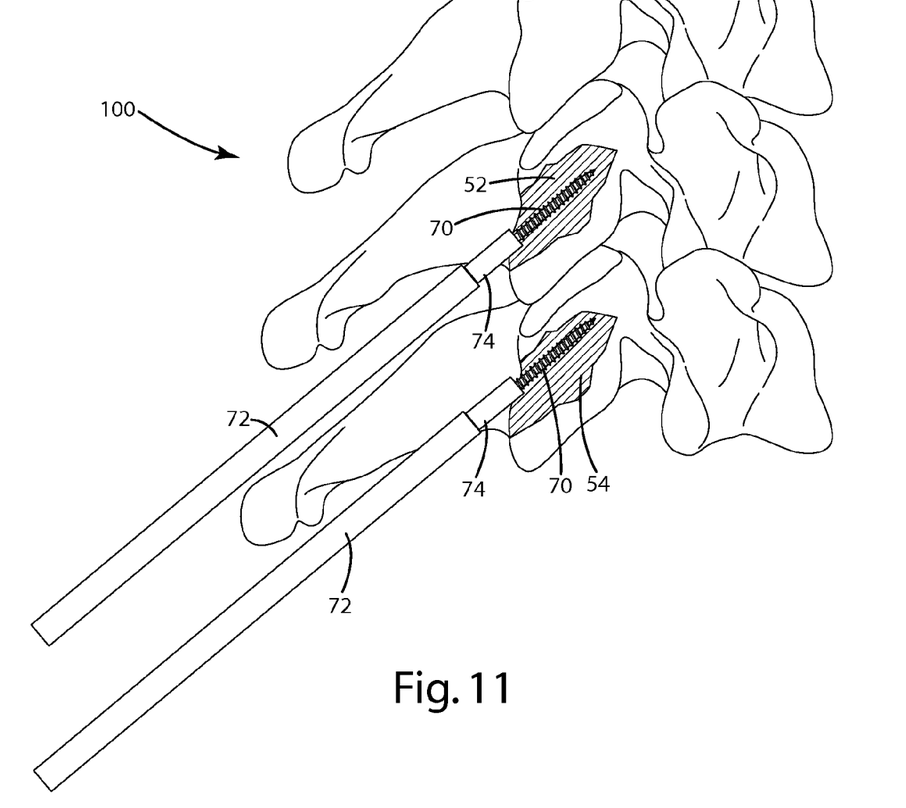
FIG. 11 is a side view of two screws in place with two attached screw towers.
Figure 12:
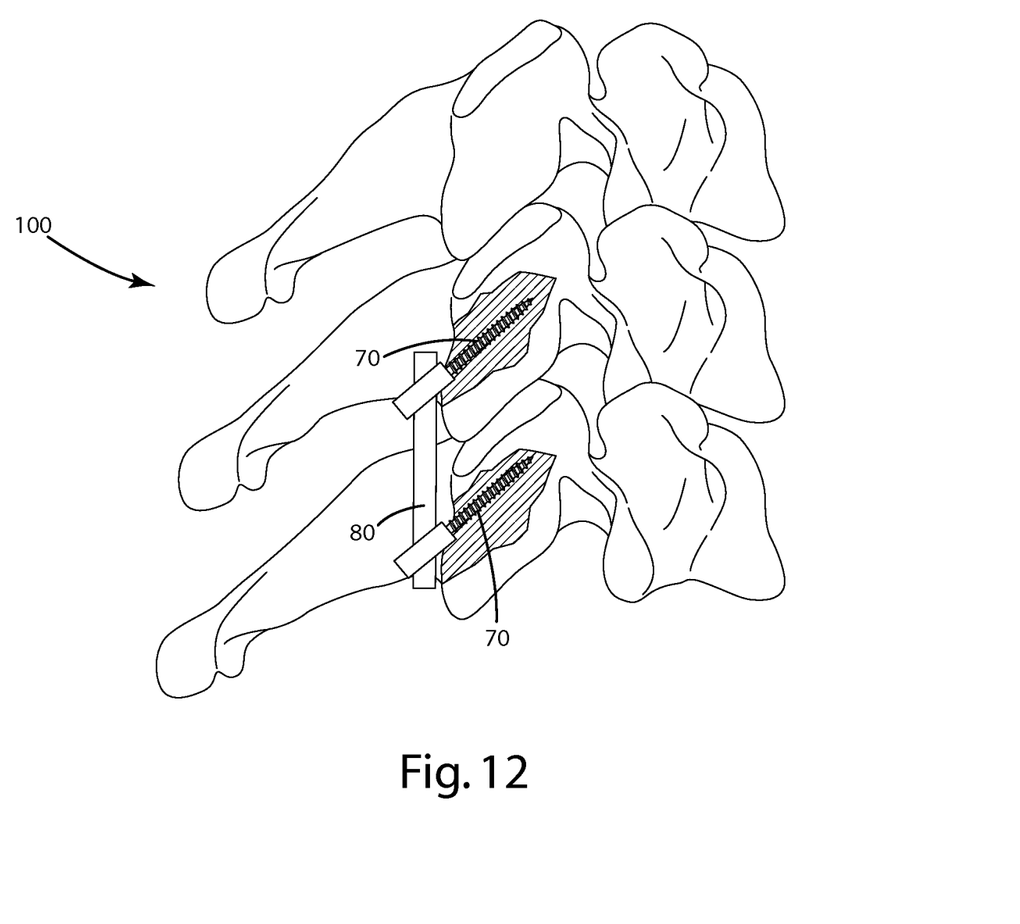
FIG. 12 is a side view of two screws in place with a rod for connecting the screws.

The screw towers 72 may retain the screws 70 in any suitable manner For example, the front ends of the towers 72 may include a recess 74 adapted to receive and retain the screws 70 so that the screws 70 extend outward from the towers 72 in a lengthwise direction, as shown in FIGS. 11 and 14. In this configuration, the screws 70 are aligned with the screw towers 72 and are ready to be inserted into the patient's spine 100. The screw towers 72 may optionally be otherwise similar to towers used in lumbar spine surgery. As shown in FIGS. 9-11, the drill 200, threaded taps and screws 70 with attached towers 72 may be inserted through the elongated tubes 38, 48 to align these surgical instruments with the elongated tubes 38, 48 and to position the surgical instruments at the proper trajectory. As shown in FIG. 12, a connector rod 80 may be positioned between the screws 70 to complete the surgery.

In a second embodiment of the invention, shown in FIGS. 13 and 14, the surgical instruments may slidably engage the handle 14 such that the cylindrical extensions 30, 40 may be eliminated from the assembly. In this configuration, each of the instruments instead has its own removable handle receiver 34', 34", 44" to guide the instrument at the proper trajectory. In this embodiment, the instruments may include attachment points, recesses or protrusions at which the guide members 32', 32", 42" may be attached to the instruments. The length and angular orientation of the guide members 32', 32", 42" may vary depending on the distance and angle desired between the handle 14 and the instruments.

Suitable materials for the assembly 8 will be known to those skilled in the art and include metal, such as stainless steel and titanium, and plastics.

II. Installation and Use

Figure 7:
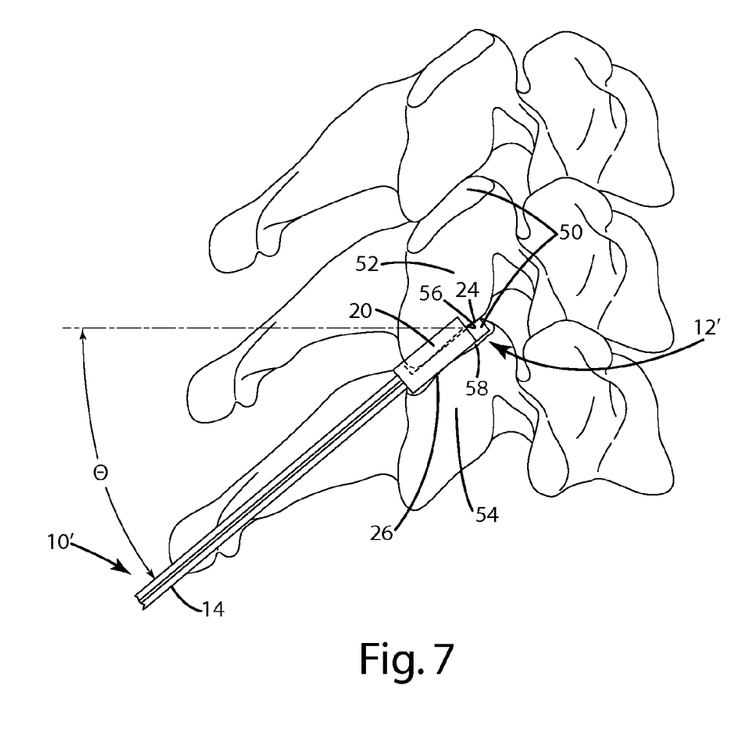
FIG. 7 is a side view of a facet sled inserted into a facet joint.
Figure 8:
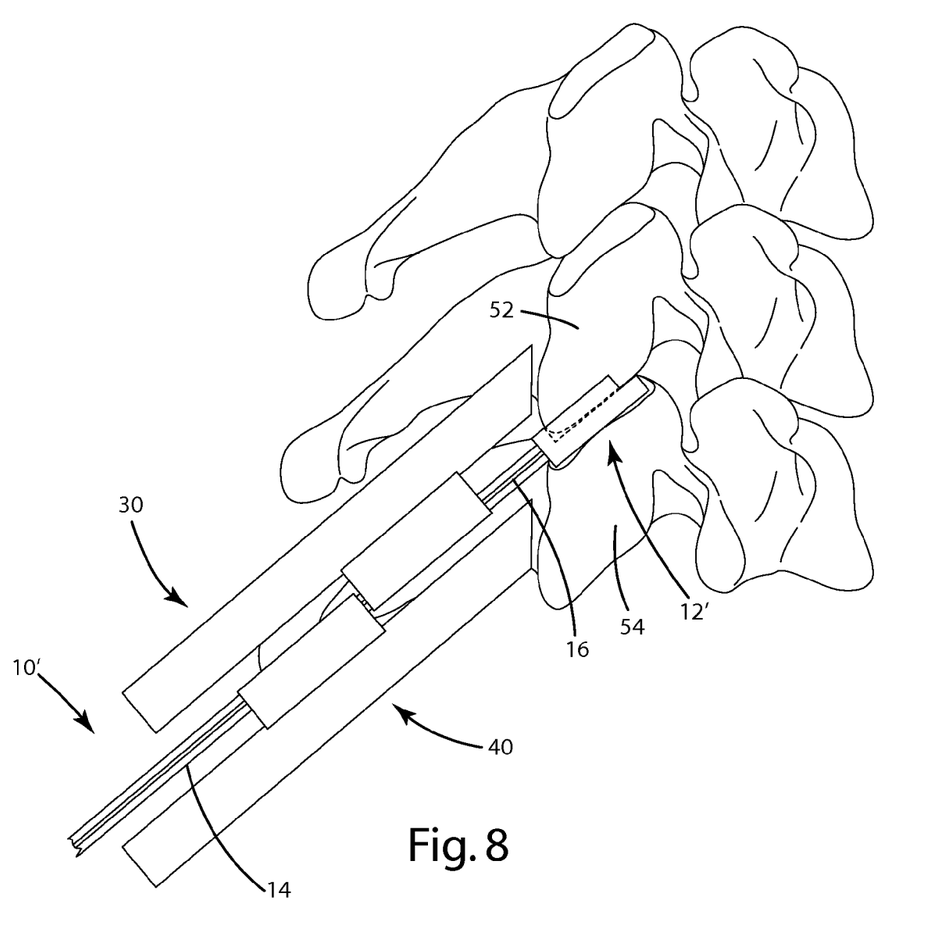
FIG. 8 is a side view of a facet sled inserted into a facet joint with a superior and an inferior cylindrical extension in place.

As shown in FIGS. 6-7, the facet sled end 12' is inserted within the facet joint 50 of the cervical spine 100, optionally using fluoroscopic guidance. The end 12' may be placed during open surgery or using minimally invasive techniques. The facet sled end 12' may also be placed in a purely percutaneous fashion or through a tubular or expandable minimally invasive retractor. As shown in FIG. 7, the sled end top surface 24 may engage the top surface 56 of the facet joint 50 and the sled end bottom surface 26 may engage the bottom surface 58 of the facet joint 50. As shown in FIG. 6, the lateral guide 20 may also engage a side surface 60 of the vertebra 52 and stop surface 22 may engage a front surface 62 of vertebra 52.

As shown in FIG. 7, the sled end 12', including top surface 24, bottom surface 26, lateral guide 20 and stop surface 22 may be sized and shaped so that placement of the end 12' in the facet joint 50 causes the handle 14 to extend outward from the spine at an angle θ, defining a trajectory into the facet complex. In the illustrated embodiment, the angle θ is a downward angle. Optionally, the angle θ may be a proper, preferred or optimum angle for screw insertion during a posterior cervical fusion surgery. Further optionally, the angle θ may be another angle based on the particular patient's bone structure. The sled end 12' may also allow for movement of the handle 14 medially or laterally (to the right and left in FIG. 6), which may allow a user to position the handle 14 at a desired medial/lateral angle about the patient's spine. Optionally, the stop surface 22 may be positioned at a predetermined angle with regard to the lateral guide 20, which may create a desired medial/lateral angle when the sled end 12' is inserted into a facet joint 50. Further optionally, the desired medial/lateral angle may be approximately 30°, which may create a diagonal trajectory for insertion of the screws 70. Inserting the screws 70 at a diagonal across the vertebrae 52, 54 may allow the user to insert longer screws 70 and therefore increase the strength of the fusion.

Once the facet sled 10, 10' is in place, the desired distance between the handle 14 and the screw placement is determined. Optionally, the desired angle between the elongated tubes 38, 48 and the handle 14 is also determined. An appropriate cylindrical extension 30, 40 (if the guide members 32, 42 are not removable) or an appropriate guide member 32, 42 (if the guide members 32, 42 are removable) may be selected based on the desired distance, desired angle between tubes 38, 48 and handle 14, and desired angle of tubes 38, 48 about the longitudinal axis 150 of the handle 14. The longitudinal axes 152, 156 of the handle receivers 34, 44 are aligned with the handle 14, shown in FIG. 5, and inserted onto the handle 14, shown in FIGS. 1 and 8. The bosses or tongues 36, 46 within the handle receivers 34, 44 may engage at least one track 16 defined in the handle 14 to maintain the handle receivers 34, 44 and elongated tubes 38, 48 at a desired angular position about the longitudinal axis 150 of the handle 14.

As shown in FIGS. 9-10, a number of instruments, including drills 200, threaded taps and screws 70 are inserted into the elongated tubes 38, 48 and are used to prepare the facet joint 50 and cervical spine 100 of the patient for placement of the screws 70. These instruments are inserted into the elongated tubes 38, 48 such that the instruments are positioned at the same angle as the elongated tubes 38, 48 with regard to the patient's spine 100.

As noted, optionally, the desired angle for the tubes 38, 48 and the instruments may be substantially parallel to the handle 14 such that the angle of the instruments is the angle θ, which is generally the proper trajectory along which the screw 70 should enter the spine 100. A drill 200 with drill bit 69 is shown in FIG. 9 inserted into the elongated tube 38 and forming a hole in vertebra 52. After the hole is formed, a threaded tap is inserted into the hole to provide threads that may engage a screw 70. Use of these instruments is known in the art and is typical during screw insertion procedures. Optionally, as shown in FIGS. 13 and 14, if a device in accordance with a second embodiment of the invention is used, the preparatory instruments may include attachment points and a user may select the appropriate guide members 32', 32", 42" such that the instruments may slide along the track 16 of the handle 14 at the desired distance, angle with respect to the handle 14 and angle about the longitudinal axis 150 of the handle 14.

To prepare the screw tower 72, the screw 70 is inserted into the end portion 74 of the screw tower 72 and the screw tower 72 is inserted into the elongated tubes 38, 48. Optionally, if a device in accordance with a second embodiment of the invention is used, one or more guide members 32", 42" may be joined with or otherwise attached to the screw tower 72 and the handle receiver 34", 44", as shown in FIG. 14. In this configuration, the screw tower 72 may slide along handle 14. As described in connection with the first embodiment above, the guide members 32", 42" may be of various configurations to provide users with various options for screw placement.

Once the facet joint 50 has been prepared for screw placement, the cylindrical extensions 30, 40 can then be selectively moved frontward and backward along the length of the handle 14. Optionally, in a second embodiment, the screw towers 72 may be moved along the length of handle 14. For example, a user could move the cylindrical extensions 30, 40 or the screw towers 72 toward the patient's spine 100 until the screw 70 engages the spine 100 and is threaded into the bone. The cylindrical extensions 30, 40 are shown in this position in FIG. 10. This process can be repeated for each screw 70, drill 200 and threaded tap that is inserted into the spine 100.

Once the screws 70 are in place, the facet sled 10, 10' and the cylindrical extensions 30, 40 may then be removed, as shown in FIG. 11. As shown in FIG. 11, the screw towers 72 may be left in place to allow manipulation of the screw heads at the level of the skin, to assist in subsequent connection of the screws 70 with a connector rod 80 and to assist with final completion of stabilization, as shown in FIG. 12. Optionally, a placement tool may be used to insert the connector rod 80 in either embodiment.

Any other conventional surgical instrumentation may be used in conjunction with the various embodiments of the present invention. This includes instruments to decorticate the bone, bone probes and reduction and compression devices.

The various embodiments of the present invention provide a posterior cervical screw system that can be readily and securely installed in a variety of surgical situations, including during open surgery, using minimally invasive techniques, using a percutaneous approach or using a tubular or expandable minimally invasive retractor. The device creates structural support for the cervical spine and allows fusion of the cervical area.

The above descriptions are those of current embodiments of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. A posterior cervical fusion surgery assembly comprising:
   a facet sled including a sled end having an anterior side, a posterior side opposite the anterior side and first and second lateral sides, said sled end being adapted to be inserted into a vertebral facet joint between a superior facet and inferior facet of a patient, the posterior side of the sled end including a guide having a height that is greater than the maximum height of the anterior side and configured to engage the posterior aspects of the superior and inferior facets and the first lateral side including a guide having a height that is greater than the maximum height of the second lateral side and configured to engage the lateral aspects of the superior and inferior facets; and an elongated handle extending from the posterior side of the sled end, the sled defining a longitudinal direction;
   a first extension slidably coupled to the elongated handle of the facet sled and configured for placement adjacent the superior facet; and
   a second extension slidably coupled coupled to the elongated handle of the facet sled and configured for placement adjacent the inferior facet;
   the first and second extensions adapted to support surgical instruments.

2. The surgical assembly of claim 1 wherein the first and second extensions include an elongated receptacle adapted to receive and guide surgical instruments.

3. The surgical assembly of claim 1 wherein the sled end includes a sled end top surface and a sled end bottom surface, the sled end top surface adapted to engage a top surface of the facet joint, the sled end bottom surface adapted to engage a bottom surface of the facet joint.

4. The surgical assembly of claim 3 wherein at least a portion of one of the sled end top surface and the sled end bottom surface includes a rasping surface.

5. The surgical assembly of claim 3 wherein the sled end top surface and the sled end bottom surface are adapted to position the sled at a desired angle with respect to a patient's spine when the sled end is inserted into the facet joint.

6. The surgical assembly of claim 5 wherein the desired angle is a proper angle for insertion of screws during the posterior cervical fusion surgery and a longitudinal axis of the at least one extension is substantially parallel to the longitudinal direction.

7. The surgical assembly of claim 6 wherein the sled end is adapted to allow a user to move the at least one extension medially and laterally about the patient's spine.

8. The surgical assembly of claim 1 wherein the sled includes an alignment means and the at least one extension includes a corresponding alignment means, the sled alignment means and the extension alignment means cooperating to maintain the at least one extension at a desired angular position with respect to the longitudinal direction.

9. The posterior cervical fusion surgery assembly of claim 1 wherein the first and second extensions are slidably removable from the sled.

* * * * *